United States Patent [19]

Bay et al.

[11] Patent Number: 4,618,719

[45] Date of Patent: Oct. 21, 1986

[54] ADDITION OF PHOSPHINES TO ALPHA-OLEFINS

[75] Inventors: W. Elliot Bay, Ridgefield, Conn.; Karl E. Reineke, Mohegan Lake, N.Y.

[73] Assignee: Stauffer Chemical Company, Westport, Conn.

[21] Appl. No.: 707,714

[22] Filed: Mar. 4, 1985

[51] Int. Cl.[4] .............................................. C07F 9/50
[52] U.S. Cl. ...................................... 568/17; 568/8; 568/14
[58] Field of Search .............................. 568/8, 14, 17

[56] References Cited

U.S. PATENT DOCUMENTS 3,322,542  5/1967  Ullmann et al. .

OTHER PUBLICATIONS

*Organic Phosphorus Compounds* by Kosolapoff and Maier, at vol. 1, pp. 61–69 (1972).
"The Preparation and Reactions of Diphenylphosphinous Chloride" by C. Stuebe et al., J. of the Amer. Chem. Soc., vol. 77, pp. 3526–3529 (1955).
"The Free Radical Addition of Phosphines to Unsaturated Compounds" by M. M. Rauhut in The Journal of Organic Chemistry, vol. 26, pp. 5138–5143 (1961).
*Organic Reactions*, edited by R. Adams et al., vol. 13, pp. 218–224 (1963).
*Methoden der Organischen Chemie* by Houben-Weyl, Organische Phosphor-Verbindungen I, vol. E1, pp. 113–119 (1982).

*Primary Examiner*—Helen M. S. Sneed

[57] ABSTRACT

There is disclosed an improved process for the addition of phospines to alpha-olefins at high yields and conversions. The process involves the absence of a catalyst whose residues could interfere with the utility of the product, such as n-hexyldiphenylphosphine, as a ligand. Simple thermal reaction is used at temperatures of at least 200° C., most preferably 250° C.–350° C. The pressure is preferably at least atmospheric. Preferred reactants, products, and processing conditions are also disclosed. Batch processes are exemplified and continuous processes proposed.

12 Claims, No Drawings

ADDITION OF PHOSPHINES TO ALPHA-OLEFINS

BACKGROUND (i) Field of the Invention

The present invention relates to the addition of phosphines to alpha-olefins, and related processes using phosphine oxides and phosphine sulfides. More particularly, the invention relates to the preparation of alkyldiphenylphosphines by a simple thermal reaction at elevated temperatures without the use of an initiator.

(ii) Prior Art

The addition reaction of alpha-olefins with phosphines is extremely well known in the art. For example, see *Organic Reactions*, edited by R. Adams et al., at Vol. 13, pgs. 218-214; *Methoden der Organischen Chemie* by Houben-Weyl, Vol. 1, pgs. 113-119; and *Organic Phosphorus Compounds* by Kosolapoff and Maier at Vol. 1, pgs. 61-68.

In general, the reaction of alpha-olefins with phosphines is normally catalyzed with bases, acids, free radical initiators, or radiation. Thermal reactions of phosphines and alpha-olefins have been noted with a few specific haloolefins without added catalysts. For example, *Organic Reactions* states " . . . phosphine has been added to several fluoroolefins at 150° C. without added catalysts. From tetrafluoroethylene a mono- and a di-adduct are obtained in addition to tetrafluoroethylene diphosphine. It is not clear whether or not these are free radical reactions." A review of the footnoted reference indicated that many other haloolefins failed to react under the same conditions. Likewise, it should be noted that Houben-Weyl has a "blank" under the catalyst column, at page 117, Table, row 1. This appears to be a typographical error since the footnoted reference apparently used a peroxide-type catalyst.

A computer search of Chemical Abstracts over the period 1967 to present, turned up only three references directed to n-hexyldiphenylphosphine and having the corresponding CA code number "RN-18298-00-5". None of these references relate to processes for preparing phosphines (or related products such as arsines), but rather to their properties and utility, as summarized below.

U.S. Pat. No. 3,322,542 (Ullmann et al) is entitled "Stabilization Additives for Photochromic Compounds". Its Example 49 relates to the use of "diphenylhexylphosphine" (DPHP) as such an additive, and a number of the other examples relate to the use of other phosphines.

"Allylic Alkylations Catalyzed by Nickel" by Cuvigny et al. in *J. Organomet. Chem.*, 250(1), C21-C24, apparently also refers to the use of hexyldiphenylphosphine as a catalyst for allylic alkylation of enolates.

"Carbon-13 NMR Spectra of Tertiary Phosphines, Arsines, and their Onium Salts" by Koketsu in *Physical Organic Chemistry*, Vol. 12, at pages 1836-43 reports the 13C-NMR spectra for compounds containing a phosphorus or arsenic atom, including alkyldiphenylphosphines such as hexyldiphenylphosphine.

"The Preparation and Reactions of Diphenylphosphinous Chloride" by C. Stuebe et al. in *J. of the Amer. Chem. Soc.*, Vol. 77, pgs. 3526-3529 (1955) includes a method of preparing hexyldiphenylphosphine at pgs. 3527-3528. It points out that diphenylphosphinous chloride reacts readily with Grignard reagents to give tertiary phosphines in good yield. From FIG. 1, a "good yield" appears to be 70-75%. It is believed that this reaction would not be easy to run on a plant scale.

"The Free Radical Addition of Phospines to Unsaturated Compounds" by M. M. Rauhut in *The Journal of Organic Chemistry*, Vol. 26, pages 5138-5143 (1961) describes the preparation of octyldiphenylphosphine by the free radical initiated addition of diphenylphosphine to 1-octene, and other related compounds. This reaction is generally low yielding and difficult to carry to completion.

Essentially, nowhere does the vast prior art appear to report an uncatalysed thermal reaction with unactivated double bonds.

SUMMARY OF THE INVENTION

In contrast to the aforementioned prior art it has now been discovered that certain species of phosphines (and their corresponding oxides and sulfides) react with alpha-olefins in high yields and conversions without the presence of a catalyst, a free radical initiator, or radiation. Mere increase in temperature to at least 200° C. has been found sufficient to form the desired product. One broad aspect of the invention is given in the independent claim hereinafter.

DESCRIPTION OF THE PREFERRED EMBODIMENTS

The preferred embodiments of the invention are shown in the claims hereinafter. They are illustrated by the Examples below contrasted with both the prior art and the Comparative Examples below. The Comparative Examples are not prior art.

Preferred phosphines (and corresponding oxides and sulfides) having utility in this invention are hereinafter alternatively called "first compound" or "C1". It is often preferred that C1 be monoreactive with only one P-H bond, such as diphenylphosphine. It is believed that C1 could be multireactive, such as phenylphosphine. When C1 is monoreactive, it preferably has the structural formula:

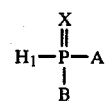

wherein: X is oxygen, sulfur or absent; A and B are individually selected from hydrogen and unsubstituted or substituted aryl, arlkyl, alkylaryl, and arylalkyl radicals; with the proviso that "essentially none of the substituents are capable of taking part in the reaction": The foregoing proviso excludes halogenated compounds. Permissible substituents include, for example, alcohols, ethers, silanes, and amines.

Preferred alpha-olefins used in this invention are hereinafter alternatively called "second compound" or C2. It is often most preferred that C2 be monoreactive with only one reactive terminal C=C bond such as a vinyl group. When C2 is multireactive it preferably has the structural formula:

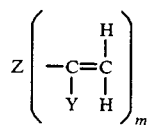

wherein: Y and Z are saturated and individually selected from hydrogen and unsubstituted or substituted alkyl and arylalkyl radicals; with the proviso that essentially none of the substituents are capable of taking part in the reaction and none are activating agents for the terminal double bond; and m is a whole number of at least one.

When a monoreactive C1 is reacted with a monoreactive C2 (as in all the Examples) the reaction product (hereinafter called "third compound" or "C3") is nearly all of a single variety. However, when C2 is a multireactive compound with multiple vinyl group, and C1 is a monoreactive compound, C3 will be a mixture of several products each of which can be represented by the structural formula:

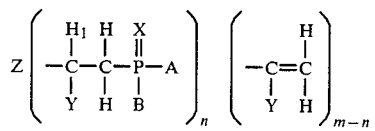

wherein: A, B, X, Y, Z and m are all as previously defined; and n is a whole number of at least one and less than m or equal to m.

When C1 and C2 are both multireactive an even larger spectrum of products becomes possible. In the limit, it should be possible to make extremely large molecules, particularly in the form of waxes. It is believed that such large molecules are likely to have low vapor pressures which may be particularly advantageous for high temperature catalyst ligands.

It is often preferred to have an excess of olefin present in order to increase the rate of reaction (see Example 6 below).

The reaction temperature, T, is at least 200° C.; preferably up to 500° C.; and most preferably in the range from 250° C. to 350° C.

The reaction pressure is preferably atmospheric or superatmospheric, preferably up to 10,000 psia; more preferably up to 1,000 psia. The particular pressure will depend mainly on the volatility of C1 and C2 at the reaction temperature and their molar ratio; and whether the pressure is controlled or autogenous.

The reaction is most preferably carried out in an inert atmosphere, for control reasons. This is essential when the desired C3 is a phosphine rather than a phosphine oxide.

A batch process may be used, as in all the Examples. It is also proposed to use a continuous process by slowly pumping a mixture of C1 and C2 into a heated tube with a flow restriction at the exit of the tube. The flow restriction will cause the necessary back pressure and residence time in the reaction tube to form the desired product. C3 could then be extruded into an inert atmosphere and the volatiles evaporated therefrom, and optionally recycled.

EXAMPLE 1

This Example illustrates the preparation of eicosyldiphenylphosphine.

To a three neck 500 ml flask was added eicosene (108 g; 0.386 mole; supplied by Shell as NEODENE 20). The flask was fitted with a magnetic stirrer, a condenser and nitrogen inlet. The eicosene had been degassed by holding at 100° C. and alternately applying vacuum and refilling the flask with nitrogen. Diphenylphosphine prepared from diphenylphosphinous chloride was in the form of a mixture containing 7% di-n-butyl ether, as residual solvent from its preparation, and 3% diphenylphosphine oxide. This diphenylphosphine mixture (77.5 g; 0.388 mole) was added by cannula. The reaction mixture was sampled for GC and infrared analysis. GC analysis indicated that 6% of the phosphine was now in the form of its oxide. The temperature of the mixture was brought to 250° C. with rapid stirring and heating. The temperature was held between 250° and 265° C. for 47 hours. Infrared analysis indicated that greater than 90% reaction of P-H (2300 cm$^{-1}$) and olefin (1650 cm$^{-1}$). The temperature was lowered to about 130° C. and the slightly cloudy, pale-yellow mixture was cannulated to a 500 ml. flask fitted with a distillation head. Volatiles were then removed at 10 mm Hg absolute pressure. The mantle temperatures ranged from 130°–328° C. Distillate temperature ranged from 167°–212° C. GC analysis (area percent) of the distillate (27.6 g) implied that the distillate contained 6.6 diphenylphosphine and 1.5 g diphenylphosphine oxide. Thus 8.1 g of original phosphine was recovered. The conversion was 89%. The residue weighed 153 g. The yield was 95% based on recovered diphenylphosphine. 12.4 g of hydrocarbons were recovered. This corresponds to a conversion of 89% and a yield of 96%.

GC analysis (area %) of the product showed that it contained:
84% eicosyldiphenylphosphine
4% eicosyldiphenylphosphine oxide
3% triphenylphosphine and its oxide (total)
5% C$_{20}$ hydrocarbon
traces of diphenylphosphine and its oxide
4% of minor unidentified components.

GC analysis (area %) of the distillate showed that it contined:
9% di-n-butyl ether
24% diphenylphosphine
5.5% diphenylphosphine oxide
19% eicosene
25% eicosane.

It is believed that the eicosane was present in the starting olefin and was not formed during the reaction. Support for this belief is found in Example 2, wherein the distillate contained very little of the corresponding material, docosane.

EXAMPLE 2

This Example illustrates the preparation of docosyldiphenylphosphine.

In a manner similar to Example 1, docosene (obtained from Aldrich) and diphenylphosphine were reacted under nitrogen at 250° C. for 27 hours. Removal of unreacted olefin and diphenylphosphine by vacuum distillation gave docosyldiphenylphosphine. The yield was 96% based on recovered olefin. The conversion was 57% based on recovered olefin.

GC analysis (area %) indicated that the starting diphenylphosphine contained about 3% oxide. It also showed that the final product contained:
90% docosyldiphenylphosphine
5% docosyldiphenylphosphine oxide
2% triphenylphosphine
traces of diphenylphosphine, docosene, and docosane.

In both Examples 1 and 2 a mixture of n-alkyl and sec-alkyl were obtained in about a ratio of 95/5.

EXAMPLE 3

This Example illustrates the preparation of hexyldiphenylphosphine.

To an annealed heavywalled PYREX glass tube was added 1-hexene (0.75 ml, 0.006 mole) and diphenylphosphine (0.10 ml, 0.0006 mole). The diphenylphosphine contained approximately 11% diphenylphosphine oxide as indicated by GC analysis. The reaction tube was attached to a vacuum line and the reaction mixture degassed by a freeze-thaw cycle. The reaction tube was sealed-off with a flame under vacuum. The tube was heated to 250° C. for 60 hours. The estimated pressure in the reaction tube was 450 psig. The reaction tube was cooled to room temperature and the seal cracked open. The excess 1-hexene was removed under vacuum. The quantity of product obtained was 0.14 g, giving a crude yield of 90%.

The GC analysis (area %) of the product showed that it contained:
74% hexyldiphenylphosphine
16% n-hexyldiphenylphosphine oxide
4% diphenylphosphine
6% of minor unidentified components.

The ratio of n-alkyl to sec-alkyl obtained was also about 95/5.

COMPARATIVE EXAMPLE 4C

Example 1 was essentially repeated except that the reaction temperature was approximately 200° C. (rather than 250° C.) and the reaction time was 46 hours (rather than 47 hours). The conversion was 30% (rather than 89%).

PROPOSED EXAMPLE 4P

Comparative Example 4C is essentially repeated except that the reaction time is 150 hours (rather than 47 hours). It is believed that the conversion would be greater than 80%.

EXAMPLE 5

Example 1 was essentially repeated, except that the reaction temperature was approximately 225° C. (instead of 250° C.) and the reaction time was 48 hours (instead of 47 hours). The conversion was about 70% (instead of 89%).

EXAMPLE 6

Example 1 was essentially repeated, except that the molar ratio of olefin/phosphine was 2/1 (instead of 1/1); the reaction temperature was 300° C. (instead of 250° C.); and the reaction time was 4½ hours (instead of 47 hours). The conversion was virtually unchanged, at about 90% (instead of 89%).

EXAMPLE 7

Example 1 was essentially repeated, except that diphenylphosphine (1.0 g, 5.4 mmoles) and eicosene (1.5 g, 5.4 mmoles) were heated under a nitrogen atmosphere for 21 hrs. at 230°–255° C. GC analysis (area %) indicated about 50% conversion of diphenylphosphine.

COMPARATIVE EXAMPLE 7C

Example 7 was essentially repeated except that a large amount (4.9 mole %) of 1,1-azobis-cyclohexanecarbonitrile (65 mg in 0.5 ml toluene) was added as a catalyst, in portions over 5 hours at 230°–255° C. Continued heating at 250°–265° C. for a further 16 hours gave about 75% conversion of the diphenylphosphine.

It will be noted that increase in reaction rate obtained in Comparative Example 7C, with a large amount of catalyst, is fairly small as compared with catalystless Example 7. Further that increase is insignificant as compared with that which can be obtained by using higher temperature and/or higher olefin/phosphine molar ratio as in Example 6.

Finally, it should be noted that, while all the foregoing Examples relate to reacting monoreactive C1 compounds with monoreactive C2 compounds, it is likely that the invention extends to corresponding compounds wherein C1 and/or C2 are multireactive compounds. In particular, C1 could be a compound containing more than one reactive P-H group; and C2 could be a compound containing more than one C=C terminal bond. Such products would also be expected to have utility as ligands.

It is further believed that at least many of the products could be advantageously made by means of a continuous process, rather than the batch process shown in all the Examples and Comparative Examples. In particular, see the dependent claims below.

It is also believed that the invention extends to corresponding compounds wherein the phosphorus atoms in C1 are replaced by arsenic atoms.

What we claim is:

1. A process for addition-reacting a phosphine first reactant with an alpha olefin second reactant by mixing said first reactant and said second reactant and heating said mixture in the absence of an initiator or catalyst at a temperature of at least 200° C. for a time and at a pressure sufficient to effect a yield of at least 50% of an alkyl diphenyl phosphine product.

2. The process of claim 1 wherein the product is eicosyldiphenylphosphine.

3. The process of claim 1 wherein the product is hexyldiphenylphosphine.

4. The process of claim 1 wherein the product is docosyldiphenylphosphine.

5. The process of claim 1 wherein the first reactant is diphenylphosphine.

6. The process of claim 1 wherein the second reactant is eicosene.

7. The process of claim 1 wherein the second reactant is docosene.

8. The process of claim 1 wherein the second reactant is 1-hexene.

9. The process of claim 1 wherein the pressure is atmospheric or superatmospheric.

10. The process of claim 9 wherein the pressure is less than 10,000 psia.

11. The process of claim 1 wherein the temperature is below 500° C.

12. The process of claim 11 wherein the temperature is in the range from 250° C. to 350° C.

* * * * *

UNITED STATES PATENT AND TRADEMARK OFFICE
CERTIFICATE OF CORRECTION

PATENT NO. : 4,618,719

DATED : October 21, 1986

INVENTOR(S) : W. Elliott Bay et al.

It is certified that error appears in the above-identified patent and that said Letters Patent are hereby corrected as shown below:

Front page (75) Inventors: "Elliot" should be --Elliott--;

Col. 3, line 20, "group" should be --groups--;

Col. 4, line 31, "6.6" should be --6.6 g--.

Signed and Sealed this

Tenth Day of March, 1987

Attest:

DONALD J. QUIGG

Attesting Officer

Commissioner of Patents and Trademarks